(12) United States Patent
Kolczewski et al.

(10) Patent No.: US 8,153,653 B2
(45) Date of Patent: Apr. 10, 2012

(54) AMIDO-TROPANE DERIVATIVES

(75) Inventors: Sabine Kolczewski, Loerrach (DE); Emmanuel Pinard, Linsdorf (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/160,559

(22) Filed: Jun. 15, 2011

(65) Prior Publication Data

US 2011/0312993 A1 Dec. 22, 2011

(30) Foreign Application Priority Data

Jun. 22, 2010 (EP) .................................. 10166757

(51) Int. Cl.
*A61K 31/44* (2006.01)
*C07D 451/02* (2006.01)

(52) U.S. Cl. ....................................... 514/304; 546/124

(58) Field of Classification Search .................. 546/124; 514/304
See application file for complete search history.

(56) References Cited

FOREIGN PATENT DOCUMENTS

WO WO2005/037783 4/2005

OTHER PUBLICATIONS

Hcaplus 1984:583457 Abstract , "Investigation on central dopaminergic receptors (D-2) using the antagonistic properties of new benzamides", Rumigny et. al., 1984.*
Gainetdinov et al., "Trends in Pharm. Sci." 23(8):367-373 (2002).
Pralong et al., "Prog. Neurobiol." 67:173-202 (2002).
Chen et al., "J. Neurophysiol." 89(2):691-703 (2003).
Tang et al., "Nature" 401:63-69 (1999).
Javitt et al., "Biol. Psychiatry" 45:668-679 (1999).
Wolkenberg et al., "Current Topics in Medical Chemistry" 10(2):170-186 (2010).
Carlsson, M. L., "J. Neural Transm." 105:525-535 (1998).
Vandenberg et al., "Exp. Opin. Ther. Targets" 5(4):507-518 (2001).
Nakazato et al., "Exp. Opin. Ther. Patents" 10(1):75-98 (2000).
Bliss et al., "Nature" 361:31-39 (1993).
Mohn et al., "Cell" 98:427-436 (1999).
Lewis et al., "Neuron" 28:325-333 (2000).
Bergereon et al., "Proc. Natl. Acad. Sci. USA" 95:15730-15734 (1998).
Armer et al., "Exp. Opin. Ther. Patents" 11(4):563-572 (2001).
Lopez-Corcuera et al., "Mol. Mem. Biol." 18:13-20 (2001).
Sharma et al., "Br. J. Psychiatry" 174(SUPPL 28):44-51 ( 1999).
"PCT International Search Report—PCT/EP2011/060073 dated Jun. 17, 2011, Mailed Aug. 8, 2011".

* cited by examiner

*Primary Examiner* — Binta Robinson
(74) *Attorney, Agent, or Firm* — George W. Johnston; Patricia S. Rocha-Tramaloni; Kimberly J. Prior

(57) ABSTRACT

The present invention relates to a compound of formula I

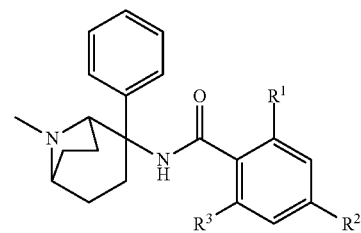

I wherein $R^1$, $R^2$ and $R^3$ are each independently hydrogen, lower alkyl, lower alkoxy, cycloalkyl, lower alkyl substituted by halogen or S-lower alkyl;

or to a pharmaceutically acceptable acid addition salt, racemic mixture, or corresponding enantiomer and/or optical isomer thereof. The compounds of formula I are good inhibitors of the glycine transporter 1 (GlyT-1), and have a good selectivity to glycine transporter 2 (GlyT-2) inhibitors. The compounds can be used in the treatment of neurological and neuropsychiatric disorders.

14 Claims, No Drawings

AMIDO-TROPANE DERIVATIVES

PRIORITY TO RELATED APPLICATION(S)

This application claims the benefit of European Patent Application No. 10166757.4, filed Jun. 22, 2010, which is hereby incorporated by reference in its entirety.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, Neuron, 2000, 28:325-33). For decades research has focused on the "dopaminergic hyperactivity" hypothesis which has led to therapeutic interventions involving blockade of the dopaminergic system (Vandenberg R J and Aubrey K R., Exp. Opin. Ther. Targets, 2001, 5(4): 507-518; Nakazato A and Okuyama S, et al., 2000, Exp. Opin. Ther. Patents, 10(1): 75-98). This pharmacological approach poorly address negative and cognitive symptoms which are the best predictors of functional outcome (Sharma T., Br. J. Psychiatry, 1999, 174 (suppl. 28): 44-51).

A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly in healthy volunteers, PCP-induced psychotomimetic action incorporates positive and negative symptoms as well as cognitive dysfunction, thus closely resembling schizophrenia in patients (Javitt D C et al., 1999, Biol. Psychiatry, 45: 668-679 and refs. herein). Furthermore transgenic mice expressing reduced levels of the NMDAR1 subunit displays behavioral abnormalities similar to those observed in pharmacologically induced models of schizophrenia, supporting a model in which reduced NMDA receptor activity results in schizophrenia-like behavior (Mohn A R et al., 1999, Cell, 98: 427-236).

Glutamate neurotransmission, in particular NMDA receptor activity, plays a critical role in synaptic plasticity, learning and memory, such as the NMDA receptors appears to serve as a graded switch for gating the threshold of synaptic plasticity and memory formation (Hebb D O, 1949, The organization of behavior, Wiley, NY; Bliss T V and Collingridge G L, 1993, Nature, 361: 31-39). Transgenic mice over-expressing the NMDA NR2B subunit exhibit enhanced synaptic plasticity and superior ability in learning and memory (Tang J P et al., 1999, Nature: 401-63-69).

Thus, if a glutamate deficit is implicate in the pathophysiology of schizophrenia, enhancing glutamate transmission, in particular via NMDA receptor activation, would be predicted to produce both anti-psychotic and cognitive enhancing effects.

The amino acid glycine is known to have at least two important functions in the CNS. It acts as an inhibitory amino acid, binding to strychnine sensitive glycine receptors, and it also influences excitatory activity, acting as an essential co-agonist with glutamate for N-methyl-D-aspartate (NMDA) receptor function. While glutamate is released in an activity-dependent manner from synaptic terminals, glycine is apparently present at a more constant level and seems to modulate/control the receptor for its response to glutamate.

One of the most effective ways to control synaptic concentrations of neurotransmitter is to influence their re-uptake at the synapses. Neurotransmitter transporters by removing neurotransmitters from the extracellular space, can control their extracellular lifetime and thereby modulate the magnitude of the synaptic transmission (Gainetdinov R R et al, 2002, Trends in Pharm. Sci., 23(8): 367-373).

Glycine transporters, which form part of the sodium and chloride family of neurotransmitter transporters, play an important role in the termination of post-synaptic glycinergic actions and maintenance of low extracellular glycine concentration by re-uptake of glycine into presynaptic nerve terminals and surrounding fine glial processes.

Two distinct glycine transporter genes have been cloned (GlyT-1 and GlyT-2) from mammalian brain, which give rise to two transporters with ~50% amino acid sequence homology. GlyT-1 presents four isoforms arising from alternative splicing and alternative promoter usage (1a, 1b, 1c and 1d). Only two of these isoforms have been found in rodent brain (GlyT-1a and GlyT-1b). GlyT-2 also presents some degree of heterogeneity. Two GlyT-2 isoforms (2a and 2b) have been identified in rodent brains. GlyT-1 is known to be located in CNS and in peripheral tissues, whereas GlyT-2 is specific to the CNS. GlyT-1 has a predominantly glial distribution and is found not only in areas corresponding to strychnine sensitive glycine receptors but also outside these areas, where it has been postulated to be involved in modulation of NMDA receptor function (Lopez-Corcuera B et al., 2001, Mol. Mem. Biol., 18: 13-20). Thus, one strategy to enhance NMDA receptor activity is to elevate the glycine concentration in the local microenvironment of synaptic NMDA receptors by inhibition of GlyT-1 transporter (Bergereon R. Et al., 1998, Proc. Natl. Acad. Sci. USA, 95: 15730-15734; Chen L et al., 2003, J. Neurophysiol., 89 (2): 691-703).

Glycine transporters inhibitors are suitable for the treatment of neurological and neuropsychiatric disorders. The majority of diseases states implicated are psychoses, schizophrenia (Armer R E and Miller D J, 2001, Exp. Opin. Ther. Patents, 11 (4): 563-572), psychotic mood disorders such as severe major depressive disorder, mood disorders associated with psychotic disorders such as acute mania or depression associated with bipolar disorders and mood disorders associated with schizophrenia, (Pralong E T et al., 2002, Prog. Neurobiol., 67: 173-202), autistic disorders (Carlsson M L, 1998, J. Neural Transm. 105: 525-535), cognitive disorders such as dementias, including age related dementia and senile dementia of the Alzheimer type, memory disorders in a mammal, including a human, attention deficit disorders and pain (Armer R E and Miller D J, 2001, Exp. Opin. Ther. Patents, 11 (4): 563-572).

Thus, increasing activation of NMDA receptors via GlyT-1 inhibition may lead to agents that treat psychosis, schizophrenia, dementia and other diseases in which cognitive processes are impaired, such as attention deficit disorders or Alzheimer's disease.

SUMMARY OF THE INVENTION

The present invention provides a compound of formula I

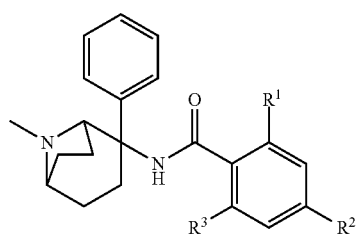

wherein

R$^1$, R$^2$ and R$^3$ are each independently hydrogen, lower alkyl, lower alkoxy, cycloalkyl, lower alkyl substituted by halogen or S-lower alkyl;

or a pharmaceutically acceptable acid addition salt, a racemic mixture, or a corresponding enantiomer and/or optical isomer thereof.

Furthermore, the present invention provides pharmaceutical compositions containing the compounds of formula I and their use in the treatment of neurological and neuropsychiatric disorders.

The compounds of formula I are good inhibitors of the glycine transporter 1 (GlyT-1), and have a good selectivity to glycine transporter 2 (GlyT-2) inhibitors.

The present invention provides the compounds of formula I per se and pharmaceutical compositions containing them. The invention also provides methods for the manufacture of the compounds of formula I and the pharmaceutical compositions of the invention. for the invention further provides methods for the treatment of diseases related to activation of NMDA receptors via Glyt-1 inhibition, for example, for the control or prevention of illnesses such as psychoses, dysfunction in memory and learning, schizophrenia, dementia and other diseases in which cognitive processes are impaired, such as attention deficit disorders or Alzheimer's disease.

The invention further provides a method for the treatment or prophylaxis of psychoses, pain, dysfunction in memory and learning, attention deficit, schizophrenia, dementia disorders or Alzheimer's disease, which method comprises administering an effective amount of a compound of formula I to a person in need thereof.

The preferred indications for using the compounds of the present invention are schizophrenia, cognitive impairment and Alzheimer's disease.

Furthermore, the invention includes all racemic mixtures, all their corresponding enantiomers and/or optical isomers.

DETAILED DESCRIPTION OF THE INVENTION

As used herein, the term "lower alkyl" denotes a saturated straight- or branched-chain hydrocarbon group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a lower alkyl group as defined above, which is attached via an O atom.

The term "cycloalkyl" denotes a saturated or partially saturated ring containing from 3 to 7 carbon atoms, for example cyclopropyl, cyclobutyl, cyclopentyl, cyclopentenyl, cyclohexyl, cyclohexenyl, cycloheptyl or cycloheptenyl. The preferred cycloalkyl ring is cyclopropyl.

The term "halogen" denotes chlorine, iodine, fluorine and bromine.

The term "lower alkyl substituted by halogen" denotes a lower alkyl group as defined above, wherein at least one hydrogen atom is replaced by a halogen atom, for example the following groups: $CF_3$, $CHF_2$, $CH_2F$, $CH_2CF_3$, $CH_2CHF_2$, $CH_2CH_2F$, $CH_2CH_2CF_3$, $CH_2CH_2CH_2CF_3$, $CH_2CH_2Cl$, $CH_2CF_2CF_3$, $CH_2CF_2CHF_2$, $CF_2CHFCF_3$, $C(CH_3)_2CF_3$, $CH(CH_3)CF_3$ or $CH(CH_2F)CH_2F$. The preferred "lower alkyl substituted by halogen" group is $CF_3$.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

One embodiment of the invention provides compounds of formula I, wherein R$^1$ is lower alkoxy, R$^2$ is lower alkyl substituted by halogen and R$^3$ is S-lower alkyl, for example the following compounds:

2-methoxy-N-((1RS,2RS,5SR)-8-methyl-2-phenyl-8-aza-bicyclo[3.2.1]oct-2-yl)-6-methylsulfanyl-4-trifluoromethyl-benzamide;

2-methoxy-N-((1S,2S,5R)-8-methyl-2-phenyl-8-aza-bicyclo[3.2.1]oct-2-yl)-6-methylsulfanyl-4-trifluoromethyl-benzamide; and 2-methoxy-N-((1R,2R,5S)-8-methyl-2-phenyl-8-aza-bicyclo[3.2.1]oct-2-yl)-6-methylsulfanyl-4-trifluoromethyl-benzamide.

A further embodiment of the invention provides compounds of formula I, wherein R$^1$ is cycloalkyl, R$^2$ is lower alkyl substituted by halogen and R$^3$ is hydrogen, for example the compound 2-cyclopropyl-N-((1RS,2RS,5SR)-8-methyl-2-phenyl-8-aza-bicyclo[3.2.1]oct-2-yl)-4-trifluoromethyl-benzamide.

An embodiment of the invention also provides compounds of formula I, wherein R$^1$ is lower alkyl, R$^2$ is lower alkyl substituted by halogen and R$^3$ is hydrogen, for example 2-ethyl-N-((1S,2S,5R) or (1R,2R,5S)-8-methyl-2-phenyl-8-aza-bicyclo[3.2.1]oct-2-yl)-4-trifluoromethyl-benzamide and 2-ethyl-N-((1R,2R,5S) or (1S,2S,5R)-8-methyl-2-phenyl-8-aza-bicyclo[3.2.1]oct-2-yl)-4-trifluoromethyl-benzamide.

A further embodiment of the invention provides compounds of formula I, wherein R$^1$ is lower alkoxy, R$^2$ is lower alkyl substituted by halogen and R$^3$ is lower alkyl, for example the compounds 2-methoxy-6-methyl-N-((1RS,2RS,5SR)-8-methyl-2-phenyl-8-aza-bicyclo[3.2.1]oct-2-yl)-4-trifluoromethyl-benzamide;

2-methoxy-6-methyl-N-((1S,2S,5R) or (1R,2R,5S)-8-methyl-2-phenyl-8-aza-bicyclo[3.2.1]oct-2-yl)-4-trifluoromethyl-benzamide;

2-methoxy-6-methyl-N-((1R,2R,5S) or (1S,2S,5R)-8-methyl-2-phenyl-8-aza-bicyclo[3.2.1]oct-2-yl)-4-trifluoromethyl-benzamide; and 2-ethyl-6-methoxy-N-((1RS,2RS,5SR)-8-methyl-2-phenyl-8-aza-bicyclo[3.2.1]oct-2-yl)-4-trifluoromethyl-benzamide.

A further embodiment of the invention provides compounds of formula I, wherein R$^1$ is lower alkoxy, R$^2$ is lower alkyl substituted by halogen and R$^3$ is cycloalkyl, for example the compounds 2-cyclopropyl-6-methoxy-N-((1RS,2RS,5SR)-8-methyl-2-phenyl-8-aza-bicyclo[3.2.1]oct-2-yl)-4-trifluoromethyl-benzamide;

2-cyclopropyl-6-methoxy-N-((1S,2S,5R) or (1R,2R,5S)-8-methyl-2-phenyl-8-aza-bicyclo[3.2.1]oct-2-yl)-4-trifluoromethyl-benzamide; and 2-cyclopropyl-6-methoxy-N-((1R,2R,5S) or (1S,2S,5R)-8-methyl-2-phenyl-8-aza-bicyclo[3.2.1]oct-2-yl)-4-trifluoromethyl-benzamide.

The present compounds of formula I and their pharmaceutically acceptable salts can be prepared by methods known in the art, for example, by processes described below, which process comprises a) reacting a compound of formula

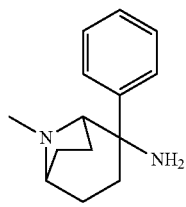

II with a compound of formula

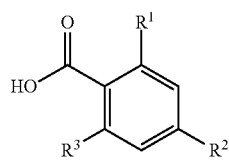

III in the presence of an activating agent such as HATU (o-(7-azabenzotriazol-1-yl)-1,1,3,3-tetramethyluronium hexafluorophosphate) or thionyl chloride
to obtain a compound of formula

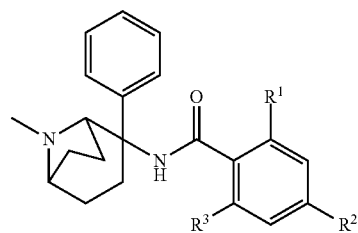

I wherein the substituents are as defined above.

The compounds of formula I can be prepared in accordance with process variant as described below and with the following scheme 1. The starting material is commercially available or can be prepared in accordance with known methods.

Compounds of general formula I can be prepared by reacting amino-tropane derivative of formula II with acid of formula III in the presence of an activating agent like HATU (o-(7-azabenzotriazol-1-yl)-1,1,3,3-tetramethyluronium hexafluorophosphate) or thionyl chloride. Amino-tropane derivatives of formula II can be prepared by reacting tropinone IV with an organo-metallic reagent like a Grignard to provide alcohol V followed by a treatment with acetonitrile in the presence of an acid like sulfuric acid to provide acetamide derivative VI which is transformed into II in the presence of an acid like HCl.

Racemic mixtures of chiral compound I can be separated using chiral HPLC.

The acid addition salts of the basic compounds of formula I can be converted to the corresponding free bases by treatment with at least a stoichiometric equivalent of a suitable base such as sodium or potassium hydroxide, potassium carbonate, sodium bicarbonate, ammonia, and the like.

EXPERIMENTAL PART

Abbreviations

HATU O-(7-azabenzotriazol-1-yl)-1,1,3,3-tetramethyluronium hexafluorophosphate
DMF Dimethylformamide
DMSO Dimethylsulfoxide
THF Tetrahydrofuran
TMEDA Tetramethylethylenediamine Scheme 1

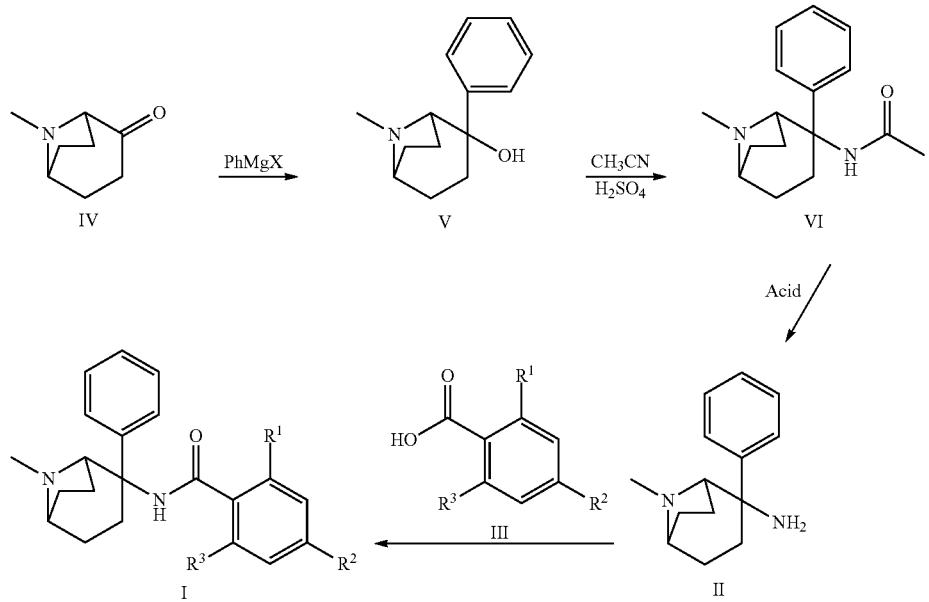

Preparation of Intermediates

EXAMPLE A.1

Preparation of (1RS,2RS,5SR)-8-Methyl-2-phenyl-8-aza-bicyclo[3.2.1]oct-2-ylamine

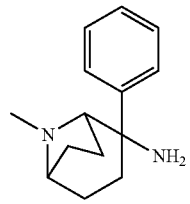

a) step 1:
8-Methyl-2-phenyl-8-aza-bicyclo[3.2.1]octan-2-ol

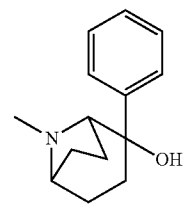

To 5.4 ml (5.39 mmol) of a 1M phenyl-magnesium bromide solution under nitrogen at 0° C., was added drop-wise a solution of 500 mg 8-methyl-8-aza-bicyclo[3.2.1]octan-2-one (CAS 78477-91-5) in 5 ml tetrahydrofuran over molsieve. The reaction mixture was stirred at 0° C. for 5 hours. The mixture was quenched under ice bath cooling with a 20% ammonium chloride solution (5 ml). The organic layer was separated and the aqueous layer was extracted once with ethyl acetate. The combined organic layers were washed with water, dried over sodium sulfate, filtered and concentrated in vacuo. The crude oil was purified with flash column chromatography on silica (20 g) eluting with a gradient formed from n-heptane and ethyl acetate (0 to 100%) to provide 508 mg (65.1%) of the title compound as a light yellow oil. MS (m/e): 218.4 (M+H$^+$).

b) step 2: N-((1RS,2RS,5SR)-8-Methyl-2-phenyl-8-aza-bicyclo[3.2.1]oct-2-yl)-acetamide

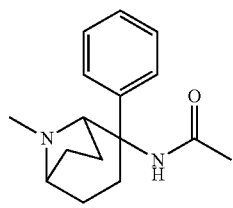

To a suspension of 210 mg (0.966 mmol) 8-methyl-2-phenyl-8-aza-bicyclo[3.2.1]octan-2-ol in 1.6 ml acetonitrile under nitrogen at 0° C., was added drop-wise 560 ul (10.43 mmol) sulfuric acid (98%) over a period of 10 minutes. The colorless solution was then stirred at room temperature for 48 hours. The solution was poured onto ice. The mixture was basified with NaOH 5N and extracted 3 times with dichloromethane. The combined extracts were dried over sodium sulfate, filtered and concentrated in vacuo. The crude colorless oil (209 mg) was purified with flash column chromatography on silica (20 g) eluting with a gradient formed from n-heptane and ethyl acetate (0 to 100%) to provide 180 mg (y: 72.1%) of the title compound as a colorless oil. MS (m/e): 259.2 (M+H$^+$).

c) step 2: (1RS,2RS,5SR)-8-Methyl-2-phenyl-8-aza-bicyclo[3.2.1]oct-2-ylamine

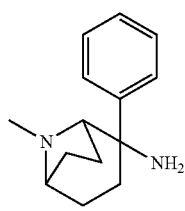

A solution of 90 mg (0.348 mmol) N-((1RS,2RS,5SR)-8-methyl-2-phenyl-8-aza bicyclo[3.2.1]oct-2-yl)-acetamide in 1.8 ml HCl 5N was heated in a 105° C. oil bath for 27 hours. The solution was cooled in an ice bath and basified with a NaOH 5N solution. The aqueous layer was extracted 3 times with dichloromethane. The combined extracts were dried over sodiumsulfate, filtered and concentrated in vacuo to provide 71 mg (y: 94.2%) of the title compound as an off-white solid. MS (m/e): 217.4 (M+H$^+$).

EXAMPLE B.1

Preparation of 2-Methoxy-6-methylsulfanyl-4-trifluoromethyl-benzoyl chloride

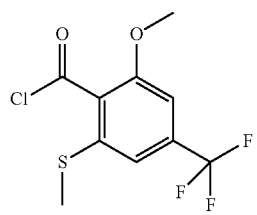

A mixture of 51 mg (0.191 mmol) 2-methoxy-6-methylsulfanyl-4-trifluoromethyl-benzoic acid (CAS 1208984-79-5) and 140 ul (1.91 mmol) thionylchloride in toluene (0.5 ml) was heated in a 80° C. oil bath for 4 hours. The solvent was removed in vacuo to provide the title compound.

EXAMPLE B.2

Preparation of 2-Cyclopropyl-4-trifluoromethyl-benzoic acid a) step 1: 2-Bromo-4-trifluoromethyl-benzoic acid methyl ester

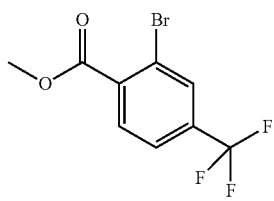

To a solution of 2 g (7.434 mmol) 2-bromo-4-trifluoromethyl-benzoic acid (CAS: 328-89-2) in 20 ml DMF under nitrogen at room temperature, was added 1.13 g (8.177 mmol) potassium carbonate and 557 ul (8.921 mmol) methyl iodide. The mixture was stirred overnight under nitrogen. The mixture was poured into water (300 ml). The aqueous layer was extracted with ethyl acetate (2×80 ml). The combined extracts were dried over sodium sulfate, filtered and concentrated in vacuo. The crude oil was purified on silica gel (Eluent: Heptane/ethyl acetate 0 to 10%) to provide 1.75 g (83%) of the title compound as an orange oil.

b) step 2: 2-Cyclopropyl-4-trifluoromethyl-benzoic acid methyl ester

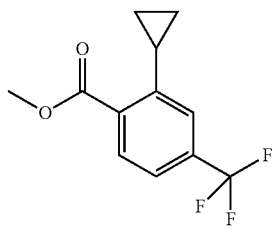

To a solution of 400 mg (1.413 mmol) 2-bromo-4-trifluoromethyl-benzoic acid methyl ester, 146 mg (1.696 mmol) cyclopropyl boronic acid, 1.21 g (4.946 mmol) tri-potassium phosphate monohydrate, 40.9 mg (0.141 mmol) tricyclohexyl phosphine in 6 ml toluene and 0.3 ml water under nitrogen at room temperature, was added 15.9 mg (0.0707 mmol) palladium acetate. The mixture was stirred in a 100° C. oil bath for 4 hours and overnight at room temperature under nitrogen. The mixture was cooled to room temperature. Water was added and the mixture extracted with ethyl acetate. The organic layer was washed once with brine, dried over sodium sulfate, filtered and concentrated in vacuo. The crude compound was purified on silica gel (Eluent: Heptane/ethyl acetate 0 to 10%) to provide 0.24 g (71%) of the title compound as a yellow oil.

c) step 3: 2-Cyclopropyl-4-trifluoromethyl-benzoic acid

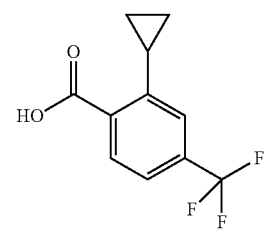

To a suspension of 485 mg (1.986 mmol) 2-cyclopropyl-4-trifluoromethyl-benzoic acid methyl ester in 8 ml ethanol at room temperature, was added 1.99 ml (3.972 mmol) 2N NaOH. The mixture was heated in an 80° C. oil bath for 30 minutes. The solution was cooled to room temperature and the ethanol was evaporated. The residue was diluted with water, acidified with 2N HCl to pH 2 and dichloromethane was added. The aqueous phase was extracted twice with dichloromethane. The combined organic phases were dried over sodium sulfate, filtered and concentrated in vacuo. The crude product was purified on silica gel (Eluent: Heptane/ethyl acetate 0 to 100%) to provide 0.197 g (27%) of the title compound as a light yellow solid. MS (m/e): 229.0 (M−H)

EXAMPLE B.3

Preparation of 2-Methoxy-6-methyl-4-trifluoromethyl-1-benzoic acid

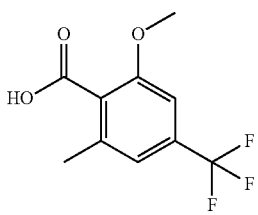

Step 1. 2,6-Dimethoxy-4-trifluoromethyl-benzoic acid

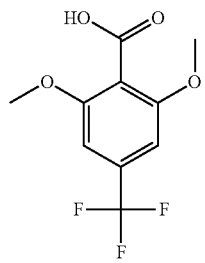

To a solution of sodium hydroxide (5.66 g, 141.4 mmol) in 33 ml water and 33 ml ethanol at room temperature under nitrogen, was added 2,6-dimethoxy-4-trifluoromethyl-benzonitrile (CAS: 51271-36-4) (3.27 g, 14.14 mmol). The reaction mixture was heated in a 90° C. oil bath for 37 hours. The reaction mixture was cooled to room temperature and 130 ml water was added. The product was collected by filtration and dried to provide 3.05 g of an off-white solid. To a solution of nitrosylsulfuric acid (15.6 g, 110.2 mmol) in 9.5 ml water at 0° C. under nitrogen, was added drop-wise a suspension of the previously obtained material in 19 ml dichloromethane. The reaction mixture was stirred at 0° C. for 4.5 h. The reaction mixture was poured over ice and extracted with dichloromethane. The combined organic layers were dried over $Na_2SO_4$, filtered and dried to provide 1.51 g of product. The aqueous phase was filtered and the white solid was dried to provide 1.36 g of product. Both batches were mixed to provide 2.87 g (93.7%) of the title compound as a white solid. MS (m/e): 249.1 (M−H).

Step 2. 2,6-Dimethoxy-4-trifluoromethyl-benzoyl chloride

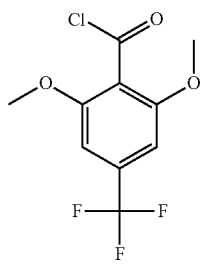

To a suspension of 14.47 g (57.84 mmol) 2,6-dimethoxy-4-trifluoromethyl-benzoic acid in 160 ml toluene containing four drops DMF under nitrogen at room temperature, was added 42 ml (578.4 mmol) thionyl chloride. The mixture was heated in a 85° C. oil bath for 3 hours. The solvent was removed in vacuo to provide 15.37 g (yield: 98.9%) of the title compound as an off-white solid.

Step 3. N-(2-Hydroxy-1,1-dimethyl-ethyl)-2,6-dimethoxy-4-trifluoromethyl-benzamide

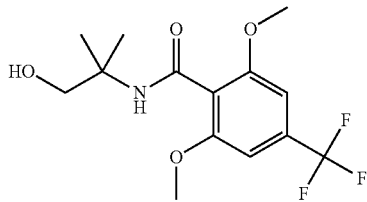

To a solution of 3.7 ml (37.22 mmol) 2-amino-2-methyl-1-propanol in 42 ml dichloromethane under nitrogen at 0° C., was added drop-wise a solution of 5 g (18.61 mmol) 2,6-dimethoxy-4-trifluoromethyl-benzoyl chloride in 12 ml dichloromethane. The temperature rose to 7° C. The mixture was stirred at room temperature for 4 hours. The mixture was poured onto 75 ml water. The organic layer was separated and the aqueous layer was extracted twice with dichloromethane. The combined organic layers were washed with brine, dried over sodium sulfate, filtered and concentrated in vacuo to provide 5.66 g (yield: 94.6%) of the title compound as a yellow solid. MS (m/e): 322.2 (M+H$^+$).

Step 4. 2-(2,6-Dimethoxy-4-trifluoromethyl-phenyl)-4,4-dimethyl-4,5-dihydro-oxazole

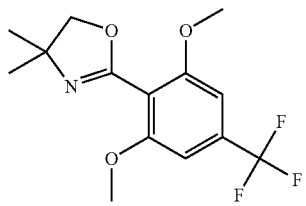

A solution of 5.66 g (17.62 mmol) N-(2-hydroxy-1,1-dimethyl-ethyl)-2,6-dimethoxy-4-trifluoromethyl-benzamide in 60 ml dichloromethane was cooled to 10° C. 3.8 ml (52.85 mmol) thionylchloride was added drop-wise. The temperature rose to 15° C. The mixture was stirred at room temperature for 1 hour. The solution was added drop-wise to 130 ml of a cooled 2M sodium carbonate solution. The emulsion was diluted with water and filtered, to remove the white solid. The organic layer was separated and the aqueous layer was extracted twice with dichloromethane. The combined extracts were dried over sodium sulfate, filtered and concentrated in vacuo. The crude light yellow solid (5.27 g) was purified with flash column chromatography on silica (70 g) eluting with a gradient formed from n-heptane and ethyl acetate (0 to 50%) to provide 4.8 g (yield: 89.8%) of the title compound as a white solid. MS (m/e): 304.2 (M+H$^+$).

Step 5. 2-(2-Methoxy-6-methyl-4-trifluoromethyl-phenyl)-4,4-dimethyl-4,5-dihydro-oxazole

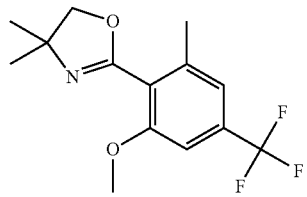

To a 0° C. solution of 1.5 g (4.946 mmol) 2-(2,6-dimethoxy-4-trifluoromethyl-phenyl)-4,4-dimethyl-4,5-dihydro-oxazole in 9 ml tetrahydrofuran over mol-sieve, was added drop-wise 9.89 ml (29.68 mmol) of a 3M methylmagnesium bromide solution in diethyl ether maintaining the temperature below 5° C. The mixture was allowed to warm to room temperature and then was heated in a 70° C. oil bath for 24 hours. The mixture was cooled in an ice bath and quenched with 60 ml of a saturated ammonium solution. Ethyl acetate was added. The organic layer was separated and the aqueous layer was extracted once with ethyl acetate. The combined extracts were dried over sodium sulfate, filtered and concentrated in vacuo. The crude orange oil (1.38 g) was purified with flash column chromatography on silica eluting with a gradient formed from n-heptane and ethyl acetate (0 to 35%) to provide 419 mg (yield: 31.2%) of 2-(2,6-dimethyl-4-trifluoromethyl-phenyl)-4,4-dimethyl-4,5-dihydro-oxazole as a white solid. MS (m/e): 272.2 (M+H$^+$) and 532 mg (yield: 37.4%) of the title compound as a colorless oil. MS (m/e): 288.1 (M+H$^+$)

Step 6. 2-Methoxy-6-methyl-4-trifluoromethyl-benzoic acid 2-methyl-2-nitro-propyl ester

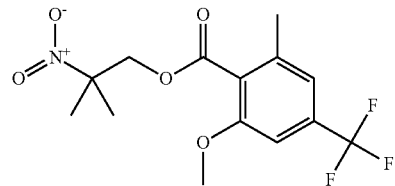

To a solution of 330 mg (1.149 mmol) 2-(2-methoxy-6-methyl-4-trifluoromethyl-phenyl)-4,4-dimethyl-4,5-dihydro-oxazole in 14 ml acetonitrile was added 11.5 ml (0.0046 mmol) of an 0.4 mM aqueous Na2-EDTA solution at room temperature. 1.05 ml (11.49 mmol) 1,1,1-trifluoroacetone was added at once with a pre-cooled syringe. A mixture of 2.9 g (34.47 mmol) NaHCO$_3$ and 7.06 g (11.49 mmol) oxone was added portion-wise over a period of 15 minutes. The mixture was stirred for 30 minutes. The reaction mixture was diluted with 70 ml water. The aqueous layer was extracted 3 times with dichloromethane. The combined extracts were dried over sodium sulfate, filtered and concentrated in vacuo to provide 388 mg (y: 101%) of the title compound as a colorless oil.

Step 7.
2-Methoxy-6-methyl-4-trifluoromethyl-1-benzoic acid

To a solution of 385 mg (1.148 mmol) 2-methoxy-6-methyl-4-trifluoromethyl-benzoic acid 2-methyl-2-nitro-propyl ester in 3.8 ml dioxane was added 2.3 ml (11.48 mmol) of an 5M aqueous NaOH solution. The mixture was heated in an 100° C. oil bath for 24 hours. The dioxane was removed in vacuo. The residue was diluted with water and extracted twice with ethyl acetate. The aqueous layer was acidified with HCl 5N and extracted 3 times with dichloromethane. The combined dichloromethane extracts were dried over sodium sulfate, filtered and concentrated in vacuo to provide 243 mg (y: 90.4%) of the title compound as a light yellow solid. MS (m/e): 232.9 (M−H).

EXAMPLE B.4
Preparation of 2-cyclopropyl-6-methoxy-4-trifluoromethyl-benzoic acid

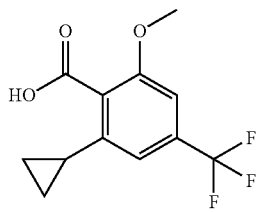

The title compound, off-white solid, MS: m/e=258.9 (M−H), was prepared according to the procedure described for intermediate B3 from 2-(2,6-dimethoxy-4-trifluoromethyl-phenyl)-4,4-dimethyl-4,5-dihydro-oxazole using cyclopropyl-magnesium bromide as a Grignard reagent

EXAMPLE B.5
Preparation of 2-Ethyl-6-methoxy-4-trifluoromethyl-benzoic acid

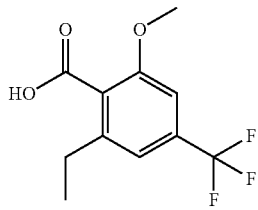

The title compound, light yellow solid, MS: m/e=247.0 (M−H), was prepared according to the procedure described for intermediate B3 from 2-(2,6-dimethoxy-4-trifluoromethyl-phenyl)-4,4-dimethyl-4,5-dihydro-oxazole using ethyl-magnesium bromide as a Grignard reagent

DESCRIPTION OF ACTIVE EXAMPLES

Example 1

2-Methoxy-N-((1RS,2RS,5SR)-8-methyl-2-phenyl-8-aza-bicyclo[3.2.1]oct-2-yl)-6-methylsulfanyl-4-trifluoromethyl-benzamide

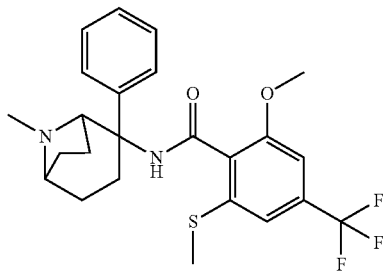

To a solution of (1RS,2RS,5SR)-8-methyl-2-phenyl-8-aza-bicyclo[3.2.1]oct-2-ylamine (intermediate A1) (670 mg, 3.1 mmol) in dichloromethane (10 ml) under nitrogen at room temperature, was added N,N-diisopropylethylamine (1.23 g, 1.61 ml, 9.29 mmol), followed drop-wise by a solution of 2-methoxy-6-(methylthio)-4-(trifluoromethyl)benzoyl chloride (intermediate B1) (970 mg, 3.41 mmol) in dichloromethane (7 ml). The reaction mixture was stirred at room temperature for 2 hours. The solution was washed once with a 2M sodium carbonate solution. The aqueous layer was extracted once with dichloromethane. The combined organic layers were dried over sodium sulfate, filtered and concentrated in vacuo. The crude yellow oil (2.04 g), which crystallized in the fridge, was suspended in diethyl ether. The white precipitate was filtered and rinsed with diethyl ether to provide 1.16 g (y: 80.6%) of the title compound as a white solid. MS (m/e): 465.2 (M+H⁺).

The examples 2 and 3 have been prepared by separation of the corresponding racemic material by chiral HPLC:

| Expl. No. | Structure | Systematic Name | Starting racemic material | Retention time (min.)* | MW found MH⁺ |
|---|---|---|---|---|---|
| 2 | 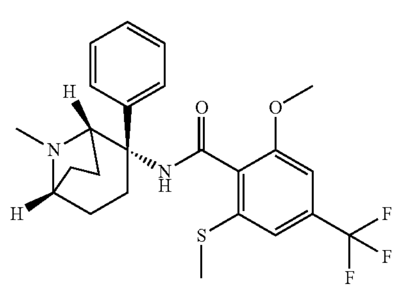 | 2-Methoxy-N-((1S,2S,5R)-8-methyl-2-phenyl-8-aza-bicyclo[3.2.1]oct-2-yl)-6-methylsulfanyl-4-trifluoromethyl-benzamide | 2-Methoxy-N-((1RS,2RS,5SR)-8-methyl-2-phenyl-8-aza-bicyclo[3.2.1]oct-2-yl)-6-methylsulfanyl-4-trifluoromethyl-benzamide (example 1) | 6.3 | 465.2 |

-continued

| Expl. No. | Structure | Systematic Name | Starting racemic material | Retention time (min.)* | MW found MH+ |
|---|---|---|---|---|---|
| 3 | 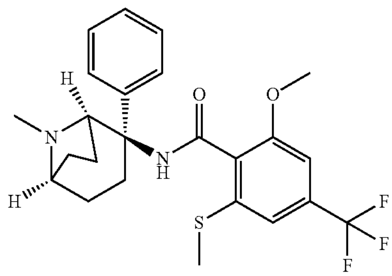 | 2-Methoxy-N-((1R,2R,5S)-8-methyl-2-phenyl-8-aza-bicyclo[3.2.1]oct-2-yl)-6-methylsulfanyl-4-trifluoromethyl-benzamide | 2-Methoxy-N-((1RS,2RS,5SR)-8-methyl-2-phenyl-8-aza-bicyclo[3.2.1]oct-2-yl)-6-methylsulfanyl-4-trifluoromethyl-benzamide (example 1) | 9.5 | 465.2 |

*: Analytical separation conditions, eluent: 15 % Isopropanol/Heptane

Example 4

2-Cyclopropyl-N-((1RS,2RS,5SR)-8-methyl-2-phenyl-8-aza-bicyclo[3.2.1]oct-2-yl)-4-trifluoromethyl-benzamide

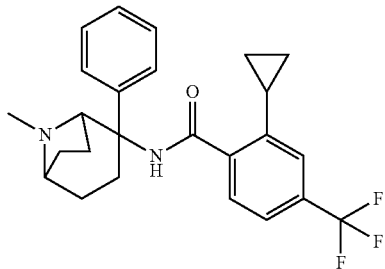

To a solution of 23.4 mg (0.102 mmol) 2-cyclopropyl-4-trifluoromethyl-benzoic acid (intermediate B2), 53.1 mg (0.139 mmol) HATU and 64 ul (0.370 mmol) N-ethyldiisopropylamine in 0.8 ml N,N-dimethylformamide, was added a solution of 20 mg (0.0925 mmol) (1RS,2RS,5SR)-8-methyl-2-phenyl-8-aza-bicyclo[3.2.1]oct-2-ylamine (intermediate A1) in 0.2 ml N,N-dimethylformamide. The mixture was stirred at room temperature overnight. The solvent was removed in vacuo. The residue was dissolved in ethyl acetate. The solution was washed once with water and twice with a saturated sodium bicarbonate solution. The aqueous layer was extracted once with ethyl acetate. The combined extracts were dried over sodium sulfate, filtered and concentrated in vacuo. The crude oil was purified with flash column chromatography on silica (5 g) eluting with a gradient formed from n-heptane and ethyl acetate (0 to 50%) to provide 10 mg (y: 25.2%) of the title compound as a colorless viscous oil. MS (m/e): 429.2 (M+H+)

The examples 5 and 6 have been prepared by separation of the corresponding racemic material: 2-ethyl-N-((1RS,2RS,5SR)-8-methyl-2-phenyl-8-aza-bicyclo[3.2.1]oct-2-yl)-4-trifluoromethyl-benzamide by chiral HPLC as indicated below. 2-Ethyl-N-((1RS,2RS,5SR)-8-methyl-2-phenyl-8-aza-bicyclo[3.2.1]oct-2-yl)-4-trifluoromethyl-benzamide, light yellow gum, MS (m/e): 417.3 (M+H+) was prepared according to the procedure described for example 4 from (1RS,2RS,5SR)-8-methyl-2-phenyl-8-aza-bicyclo[3.2.1]oct-2-ylamine (intermediate A1) and 2-ethyl-4-trifluoromethyl-benzoic acid (CAS: 854531-63-8).

| Expl. No. | Structure | Systematic Name | Starting racemic material | Retention time (min.)* | MW found (MH+) |
|---|---|---|---|---|---|
| 5 | 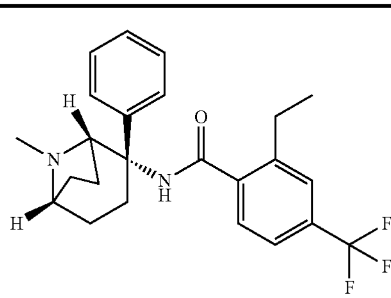 | 2-Ethyl-N-((1S,2S,5R) or (1R,2R,5S)-8-methyl-2-phenyl-8-aza-bicyclo[3.2.1]oct-2-yl)-4-trifluoromethyl-benzamide | 2-ethyl-N-((1RS,2RS,5SR)-8-methyl-2-phenyl-8-aza-bicyclo[3.2.1]oct-2-yl)-4-trifluoromethyl-benzamide | 6.3 | 417.3 |

| Expl. No. | Structure | Systematic Name | Starting racemic material | Retention time (min.)* | MW found (MH+) |
|---|---|---|---|---|---|
| 6 | 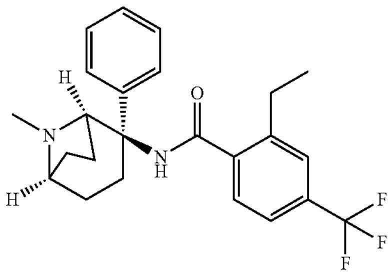 | 2-Ethyl-N-((1R,2R,5S) or (1S,2S,5R)-8-methyl-2-phenyl-8-aza-bicyclo[3.2.1]oct-2-yl)-4-trifluoromethyl-benzamide | 2-ethyl-N-((1RS,2RS,5SR)-8-methyl-2-phenyl-8-aza-bicyclo[3.2.1]oct-2-yl)-4-trifluoromethyl-benzamide | 14.2 | 417.3 |

*: Analytical separation conditions, eluent: 15 % Isopropanol/Heptane

Example 7

2-Methoxy-6-methyl-N-((1RS,2RS,5SR)-8-methyl-2-phenyl-8-aza-bicyclo[3.2.1]oct-2-yl)-4-trifluoromethyl-benzamide

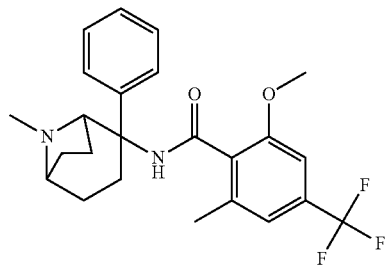

Title compound, off-white foam, MS (m/e): 433.4 (M+H+) was prepared according to the procedure described for example 4 from (1RS,2RS,5SR)-8-methyl-2-phenyl-8-aza-bicyclo[3.2.1]oct-2-ylamine (intermediate A1) and 2-methoxy-6-methyl-4-trifluoromethyl-1-benzoic acid (intermediate B3).

The examples 8 and 9 have been prepared by separation of the corresponding racemic material by chiral HPLC:

| Expl. No. | Structure | Systematic Name | Starting racemic material | Retention time (min.)* | MW found (MH+) |
|---|---|---|---|---|---|
| 8 | 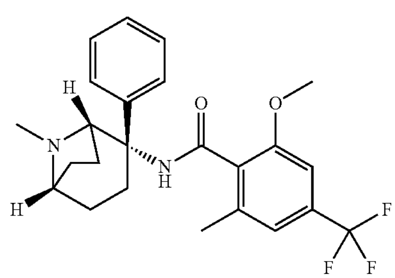 | 2-Methoxy-6-methyl-N-((1S,2S,5R) or (1R,2R,5S)-8-methyl-2-phenyl-8-aza-bicyclo[3.2.1]oct-2-yl)-4-trifluoromethyl-benzamide | 2-Methoxy-6-methyl-N-(1RS,2RS,5SR)-8-methyl-2-phenyl-8-aza-bicyclo[3.2.1]oct-2-yl)-4-trifluoromethyl-benzamide | 6.0 | 433.4 |
| 9 | 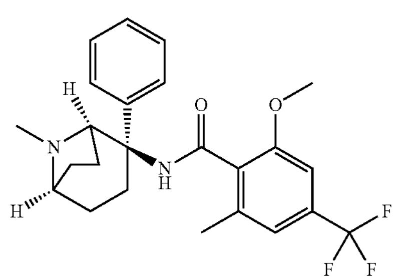 | 2-Methoxy-6-methyl-N-((1R,2R,5S) or (1S,2S,5R)-8-methyl-2-phenyl-8-aza-bicyclo[3.2.1]oct-2-yl)-4-trifluoromethyl-benzamide | 2-Methoxy-6-methyl-N-((1RS,2RS,5SR)-8-methyl-2-phenyl-8-aza-bicyclo[3.2.1]oct-2-yl)-4-trifluoromethyl-benzamide | 13.3 | 433.4 |

*: Analytical separation conditions, eluent: 15 % Isopropanol/Heptane

Example 10

2-Cyclopropyl-6-methoxy-N-((1RS,2RS,5SR)-8-methyl-2-phenyl-8-aza-bicyclo[3.2.1]oct-2-yl)-4-trifluoromethyl-benzamide

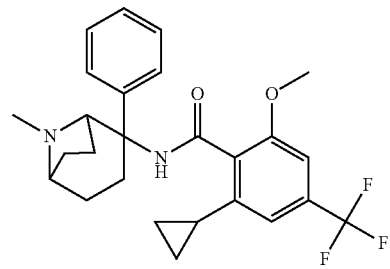

Title compound, off-white foam, MS (m/e): 459.3 (M+H$^+$) was prepared according to the procedure described for example 4 from (1RS,2RS,5SR)-8-methyl-2-phenyl-8-aza-bicyclo[3.2.1]oct-2-ylamine (intermediate A1) and 2-cyclopropyl-6-methoxy-4-trifluoromethyl-benzoic acid (intermediate B4).

The examples 11 and 12 have been prepared by separation of the corresponding racemic material by chiral HPLC:

Example 13

2-Ethyl-6-methoxy-N-((1RS,2RS,5SR)-8-methyl-2-phenyl-8-aza-bicyclo[3.2.1]oct-2-yl)-4-trifluoromethyl-benzamide

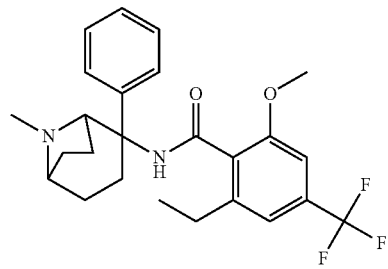

Title compound, light yellow gum, MS (m/e): 447.3 (M+H$^+$) was prepared according to the procedure described for example 4 from (1RS,2RS,5SR)-8-methyl-2-phenyl-8-aza-bicyclo[3.2.1]oct-2-ylamine (intermediate A1) and 2-ethyl-6-methoxy-4-trifluoromethyl-benzoic acid (intermediate B5).

The compounds of formula I and their pharmaceutically usable addition salts possess valuable pharmacological properties. Specifically, the compounds of the present invention are good inhibitors of the glycine transporter I (GlyT-1).

The compounds were investigated in accordance with the test given hereinafter.

| Expl. No. | Structure | Systematic Name | Starting racemic material | Retention time (min.)* | MW found (MH$^+$) |
|---|---|---|---|---|---|
| 11 | 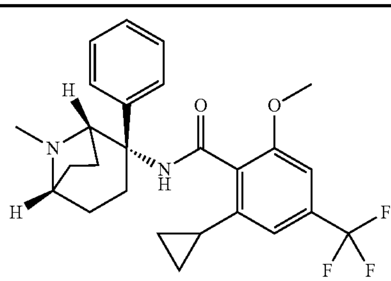 | 2-Cyclopropyl-6-methoxy-N-((1S,2S,5R) or (1R,2R,5S)-8-methyl-2-phenyl-8-aza-bicyclo[3.2.1]oct-2-yl)-4-trifluoromethyl-benzamide | 2-Cyclopropyl-6-methoxy-N-((1RS,2RS,5SR)-8-methyl-2-phenyl-8-aza-bicyclo[3.2.1]oct-2-yl)-4-trifluoromethyl-benzamide | 5.3 | 459.3 |
| 12 | 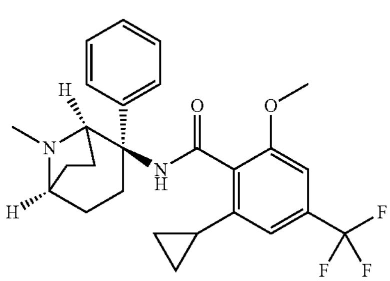 | 2-Cyclopropyl-6-methoxy-N-((1R,2R,5S) or (1S,2S,5R)-8-methyl-2-phenyl-8-aza-bicyclo[3.2.1]oct-2-yl)-4-trifluoromethyl-benzamide | 2-Cyclopropyl-6-methoxy-N-((1RS,2RS,5SR)-8-methyl-2-phenyl-8-aza-bicyclo[3.2.1]oct-2-yl)-4-trifluoromethyl-benzamide | 11.1 | 459.3 |

*: Analytical separation conditions, eluent: 15 % Isopropanol/Heptane

Solutions and Materials

DMEM complete medium: Nutrient mixture F-12 (Gibco Life-technologies), fetal bovine serum (FBS) 5%, (Gibco life technologies), Penicillin/Streptomycin 1% (Gibco life technologies), Hygromycin 0.6 mg/ml (Gibco life technologies), Glutamine 1 mM Gibco life technologies) Uptake buffer (UB): 150 mM NaCl, 10 mM Hepes-Tris, pH 7.4, 1 mM $CaCl_2$, 2.5 mM KCl, 2.5 mM $MgSO_4$, 10 mM (+) D-glucose. Flp-in™-CHO (Invitrogen Cat n° R758-07) cells stably transfected with mGlyT1b cDNA.

Glycine Uptake Inhibition Assay (mGlyT-1b)

On day 1 mammalian cells, (Flp-in™-CHO), transfected with mGlyT-1b cDNA, were plated at the density of 40,000 cells/well in complete F-12 medium, without hygromycin in 96-well culture plates. On day 2, the medium was aspirated and the cells were washed twice with uptake buffer (UB). The cells were then incubated for 20 min at 22° C. with either (i) no potential competitor, (ii) 10 mM non-radioactive glycine, (iii) a concentration of a potential inhibitor. A range of concentrations of the potential inhibitor was used to generate data for calculating the concentration of inhibitor resulting in 50% of the effect (e.g. $IC_{50}$, the concentration of the competitor inhibiting glycine uptake of 50%). A solution was then immediately added containing [$^3$H]-glycine 60 nM (11-16 Ci/mmol) and 25 µM non-radioactive glycine. The plates were incubated with gentle shaking and the reaction was stopped by aspiration of the mixture and washing (three times) with ice-cold UB. The cells were lysed with scintillation liquid, shaken 3 hours and the radioactivity in the cells was counted using a scintillation counter.

The compounds described in the examples have an $IC_{50}$ data <1.0 µM. The $IC_{50}$ data for representative compounds (<0.2 µM) is provided in table 1.

TABLE 1

| Example | $IC_{50}$ data (µM) |
|---|---|
| 1 | 0.014 |
| 2 | 0.021 |
| 3 | 0.008 |
| 4 | 0.008 |
| 5 | 0.019 |
| 6 | 0.031 |
| 7 | 0.006 |
| 8 | 0.02 |
| 9 | 0.02 |
| 10 | 0.004 |
| 11 | 0.006 |
| 12 | 0.006 |
| 13 | 0.014 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Compositions containing a compound of formula I or a pharmaceutically acceptable salt thereof and a therapeutically inert carrier are also encompassed by the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

The most preferred indications in accordance with the present invention are those, which include disorders of the central nervous system, for example the treatment or prevention of schizophrenia, cognitive impairment and Alzheimer's disease.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of formula I or of the corresponding amount of a pharmaceutically acceptable salt thereof. The daily dosage can be administered as single dose or in divided doses and, in addition, the upper limit can also be exceeded when this is found to be indicated.

| Tablet Formulation (Wet Granulation) | | | | |
|---|---|---|---|---|
| | | mg/tablet | | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.

2. Dry the granules at 50° C.

3. Pass the granules through suitable milling equipment.

4. Add item 5 and mix for three minutes; compress on a suitable press.

| Capsule Formulation | | | | |
|---|---|---|---|---|
| | | mg/capsule | | |
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The invention claimed is:
1. A compound of formula I wherein
R$^1$, R$^2$ and R$^3$ are each independently hydrogen, lower alkyl, lower alkoxy, cycloalkyl, lower alkyl substituted by halogen or S-lower alkyl;
or a pharmaceutically acceptable acid addition salt, or corresponding enantiomer or optical isomer thereof.

2. The compound of claim 1, wherein R$^1$ is lower alkoxy, R$^2$ is lower alkyl substituted by halogen and R$^3$ is S-lower alkyl.

3. The compound of claim 2, wherein the compound is
2-methoxy-N-((1RS,2RS,5SR)-8-methyl-2-phenyl-8-aza-bicyclo[3.2.1]oct-2-yl)-6-methylsulfanyl-4-trifluoromethyl-benzamide;
2-methoxy-N-((1S,2S,5R)-8-methyl-2-phenyl-8-aza-bicyclo[3.2.1]oct-2-yl)-6-methylsulfanyl-4-trifluoromethyl-benzamide; or
2-methoxy-N-((1R,2R,5S)-8-methyl-2-phenyl-8-aza-bicyclo[3.2.1]oct-2-yl)-6-methylsulfanyl-4-trifluoromethyl-benzamide.

4. The compound of claim 1, wherein R$^1$ is cycloalkyl, R$^2$ is lower alkyl substituted by halogen and R$^3$ is hydrogen.

5. The compound of claim 4, wherein the compound is
2-cyclopropyl-N-((1RS,2RS,5 SR)-8-methyl-2-phenyl-8-aza-bicyclo[3.2.1]oct-2-yl)-4-trifluoromethyl-benzamide.

6. The compound of claim 1, wherein R$^1$ is lower alkyl, R$^2$ is lower alkyl substituted by halogen and R$^3$ is hydrogen.

7. The compound of claim 6, wherein the compound is
2-ethyl-N-((1S,2S,5R)-8-methyl-2-phenyl-8-aza-bicyclo [3.2.1]oct-2-yl)-4-trifluoromethyl-benzamide;
2-ethyl-N-((1R,2R,5S)-8-methyl-2-phenyl-8-aza-bicyclo [3.2.1]oct-2-yl)-4-trifluoromethyl-benzamide.

8. The compound of claim 1, wherein R$^1$ is lower alkoxy, R$^2$ is lower alkyl substituted by halogen and R$^3$ is lower alkyl.

9. The compound of claim 8, wherein the compound is
2-methoxy-6-methyl-N-((1RS,2RS,5 SR)-8-methyl-2-phenyl-8-aza-bicyclo[3.2.1]oct-2-yl)-4-trifluoromethyl-benzamide;
2-methoxy-6-methyl-N-((1S,2S,5R)-8-methyl-2-phenyl-8-aza-bicyclo[3.2.1]oct-2-yl)-4-trifluoromethyl-benzamide;
2-methoxy-6-methyl-N-((1R,2R,5S)-8-methyl-2-phenyl-8-aza-bicyclo[3.2.1]oct-2-yl)-4-trifluoromethyl-benzamide;
2-ethyl-6-methoxy-N-((1RS,2RS,5 SR)-8-methyl-2-phenyl-8-aza-bicyclo[3.2.1]oct-2-yl)-4-trifluoromethyl-benzamide.

10. The compound of claim 1, wherein R$^1$ is lower alkoxy, R$^2$ is lower alkyl substituted by halogen and R$^3$ is cycloalkyl.

11. The compound of claim 10, wherein the compound is
2-cyclopropyl-6-methoxy-N-((1RS,2RS,5SR)-8-methyl-2-phenyl-8-aza-bicyclo[3.2.1]oct-2-yl)-4-trifluoromethyl-benzamide;
2-cyclopropyl-6-methoxy-N-((1S,2S,5R)-8-methyl-2-phenyl-8-aza-bicyclo[3.2.1]oct-2-yl)-4-trifluoromethyl-benzamide;
2-cyclopropyl-6-methoxy-N-((1R,2R,5S)-8-methyl-2-phenyl-8-aza-bicyclo[3.2.1]oct-2-yl)-4-trifluoromethyl-benzamide.

12. A pharmaceutical composition comprising a therapeutically effective amount of a compound of formula I wherein
R$^1$, R$^2$ and R$^3$ are each independently hydrogen, lower alkyl, lower alkoxy, cycloalkyl, lower alkyl substituted by halogen or S-lower alkyl;
or a pharmaceutically acceptable acid addition salt, a racemic mixture, or corresponding enantiomer and/or optical isomer thereof and a pharmaceutically acceptable carrier.

13. A process for preparation of a compound of formula I wherein
R$^1$, R$^2$ and R$^3$ are each independently hydrogen, lower alkyl, lower alkoxy, cycloalkyl, lower alkyl substituted by halogen or S-lower alkyl;
or a pharmaceutically acceptable salt thereof;

which process comprises
reacting a compound of formula
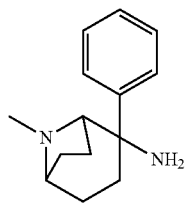
with a compound of formula
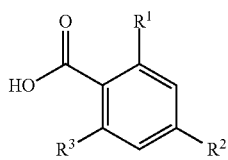
in the presence of an activating agent to obtain a compound of formula
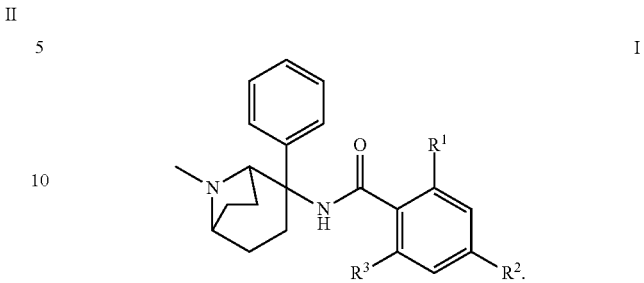
14. The process of claim 13, wherein the activating agent is HATU (o-(7-azabenzotriazol-1-yl)-1,1,3,3-tetramethyluronium hexafluorophosphate) or thionyl chloride.
* * * * *